United States Patent [19]
Hayakawa et al.

[11] Patent Number: 5,723,478
[45] Date of Patent: Mar. 3, 1998

[54] AGRICULTURAL CHEMICAL COMPOSITIONS WITH IMPROVED THIFLUZAMIDE RELEASE IN WATER

[75] Inventors: Norihito Hayakawa; Masatoshi Baba, both of Funabashi, Japan

[73] Assignee: Rohm and Haas Company, Philadelphia, Pa.

[21] Appl. No.: 804,158

[22] Filed: Feb. 20, 1997

[30] Foreign Application Priority Data

Feb. 28, 1996 [JP] Japan ................................. 8-065139

[51] Int. Cl.$^6$ ................. A01N 43/78; A01N 25/08; A01N 59/00
[52] U.S. Cl. ............. 514/365; 514/769; 514/947; 514/964; 424/409; 424/125
[58] Field of Search ......................... 424/409, 125; 514/365, 769, 947, 964

[56] References Cited

U.S. PATENT DOCUMENTS

| | | | |
|---|---|---|---|
| 4,971,796 | 11/1990 | Sjogren | 424/417 |
| 5,045,554 | 9/1991 | Alt et al. | 514/365 |
| 5,438,029 | 8/1995 | Kobata et al. | 502/430 |

OTHER PUBLICATIONS

Phillips, W.G. and Rejda–Heath, J.M., *Pesticide Science*, vol. 38, No. 1, 1993, pp. 1–7.

O'Reilly, P. et al, Brighton Crop Protection Conference—Pests and Diseases, No. 1, 1992, pp. 427–434.

*Primary Examiner*—John Pak
*Attorney, Agent, or Firm*—Thomas D. Rogerson

[57] ABSTRACT

The disclosed invention provides agricultural chemical compositions containing active carbon-treated thifluzamide as an effective ingredient. Such compositions provide increased release of thifluzamide into water.

6 Claims, No Drawings

AGRICULTURAL CHEMICAL COMPOSITIONS WITH IMPROVED THIFLUZAMIDE RELEASE IN WATER

This invention relates to an agricultural chemical composition with improved release of N-(2,6-dibromo-4-trifluoromethoxyphenyl)-2-methyl-4-trifluoromethyl-5-thiazole carboxyamide (common name: thifluzamide) in water.

Thifluzamide is a compound that has high pesticidal activity against leaf spot withering disease. Because the time to use an exterminating agent to exterminate rice leaf spot withering disease in rice plant cultivation is when the paddy field has lesser amount of water, dissolution/diffusion rate of the effective ingredient can affect the exterminating effect significantly. However, since the solubility of thifluzamide in water is extremely low, about 1.6 mg/l (20° C.), it is desirable to develop a method that enhances its rate of release in water and improves its efficacy.

We have discovered that an agricultural chemical composition containing active carbon-treated thifluzamide as its effective ingredient has an improved thifluzamide release in water, and thus the present invention was perfected.

Therefore, this invention is an agricultural chemical composition comprising thifluzamide treated with active carbon.

Another embodiment of this invention is an agricultural chemical composition wherein the active ingredient is thifluzamide obtained by dissolving thifluzamide in an organic solvent and treating the resulting solution with active carbon.

A third embodiment of this invention is a process for preparing thifluzamide with improved release in water, comprising dissolving thifluzamide in organic solvent, adding active carbon, removing the active carbon, removing the organic solvent by distillation, and crystallizing the thifluzamide.

The active carbon to be used in this invention can be of any shape and form as long as it is an active carbon in common use, such as granules and powder. There is no particular restriction about the amount to be added. The amount to be added is preferably 0.0001–0.5 part by weight, more preferably 0.001–0.5 part by weight, per one part by weight of thifluzamide in the solution.

There is no particular restriction about the organic solvent to be used in this invention, as long as it is an ordinary organic solvent that can dissolve the thifluzamide. From an industrial viewpoint, organic solvents that can dissolve more than 1.0 g of thifluzamide per 100 ml of solvent at 20° C. are preferred. For example, the following solvents can be mentioned, but use is not limited to these examples: (1)alcohols such as allyl alcohol, isobutyl alcohol, isopropyl alcohol, ethanol, tetrahydrofurfuryl alcohol, s-butanol, t-butanol, furfuryl alcohol, propargyl alcohol, 1-propanol, methanol, 3-methyl-1-pentyne-3-ol, ethyleneglycol, ethyleneglycol diacetate, ethyleneglycol diglycidyl ether, ethyleneglycol monoacetate, ethyleneglycol dimethyl ether, ethyleneglycol monoethyl ether, ethylene glycol monoethyl ether acetate, ethyleneglycol monobutyl ether, ethyleneglycol monomethyl ether, ethyleneglycol monoethyl ether acetate, ethyleneglycol monomethoxy methyl ether, ethylene chlorohydrin, glycerin, glycerin 1,3-dimethyl ether, 2-chloro-1,3-propanediol, diethyleneglycol, diethyleneglycol ethylmethyl ether, diethyleneglycol chlorohydrin, diethyleneglycol diacetate, diethyleneglycol diethyl ether, diethyleneglycol dimethyl ether, diethyleneglycol monoethyl ether, diethyleneglycol monoethyl ether acetate, diethyleneglycol monobutyl ether, diethyleneglycol monoethyl ether, dipropyleneglycol, dipropyleneglycol monoethyl ether, dipropyleneglycol monomethyl ether, tetraethyleneglycol, triethyleneglycol, triethyleneglycol monoethyl ether, triethyleneglycol monomethyl ether, trimethyleneglycol, 1,3-butanediol, 1,4-butanediol, propyleneglycol, propyleneglycol monoethyl ether, propyleneglycol monomethyl ether, and 1,5-pentanediol; (2) ethers and acetals such as diethyl ether, 1,4-dioxane, dipropyl ether, dimethyl ether, tetrahydropyrane, tetrahydrofuran, furfural, and methylal; (3) ketones such as acetone, diacetone alcohol, and methylethyl ketone; (4) esters such as ethyl formate, methyl formate, ethyl acetate, methyl acetate, ethyl lactate, methyl lactate, and γ-butyrolactone; (5) carboxylic acids such as isobutyric acid, formic acid, acetic acid, and dichloroacetic acid; (6) N-alkyl pyrrolidones such as 2-pyrrolidone, N-methyl-2-pyrrolidone, N-vinyl-2-pyrrolidone, N-ethyl-2-pyrrolidone, N-(2-hydroxyethyl)-2-pyrrolidone, N-cyclohexyl-2-pyrrolidone, N-isopropyl-2-pyrrolidone, N-(n-butyl)-2-pyrrolidone, N-(t-butyl)-2-pyrrolidone, N-(3-hydroxypropyl)-2-pyrrolidone, N-(2-methoxyethyl)-2-pyrrolidone, and N-(3-methoxypropyl)-2-pyrrolidone; and (7) others such as: allylamine, N-ethyl ethanolamine, ethylenediamine, diethylamine, N,N-dimethylformamide, N,N,N',N'-tetramethyl ethylenediamine, triethylamine, trimethylamine, pipecoline, piperidine, propylenediamine, hexamethyl phosphortriamide, monoethanolamine, acetonitrile, and dimethylsulfoxide. Preferred solvents are acetonitrile, methanol, ethanol, tetrahydrofuran, and acetone.

Even though there is no particular restriction about the form of the agent of agricultural chemical composition that employs the active carbon-treated thifluzamide of this invention as its effective ingredient, powder, hydrate, pellets, tablets, granular hydrate, suspension etc. can be mentioned for example, and each of them can be prepared by ordinary methods known to those skilled in the agricultural chemical formulation art. As to the additives other than the effective ingredient to be added in the agricultural chemical composition of this invention, there is no particular restriction.

Other effective ingredients than the active carbon-treated thifluzamide active ingredient may be added in the agricultural chemical composition of this invention.

This invention is explained embodically by way of the following Examples and Examples of Tests. However, this invention is not limited to these examples. Incidentally, "parts" shown in the following examples and comparative example mean "parts by weight".

EXAMPLE 1

Thifluzamide Treated with Active Carbon

After dissolving thifluzamide 10 g in acetonitrile 160 ml at room temperature, active carbon powder 3 g was added. After agitating for 60 minutes, it was filtered through a 1 μm filter paper. After removing acetonitrile from the filtrate by means of an evaporator, it was dried under a reduced pressure, to obtain thifliuzamide.

EXAMPLE 2

Thifluzamide Treated with Active Carbon

After dissolving thifluzamide 10 g in acetonitrile 160 ml at room temperature, active carbon powder 0.5 g was added. After agitating for 60 minutes, it was filtered through a 1 μm filter paper. After removing acetonitrile from the filtrate by means of an evaporator, it was dried under a reduced pressure, to obtain thifluzamide.

EXAMPLE 3

Pellet 1

Thifluzamide obtained in Example 1 was fractured by means of a jet crusher (A-O Jet Mill, manufactured by Seishin Kigyo K. K.). This fractured material 2.0 parts, sodium lignin sulfonate 5.0 parts, alkylbenzene sulfonic acid 0.5 part, sodium polyacrylate, 1.0 part, sodium tripolyphosphate 2.0 parts, bentonite 40 parts, calcium carbonate 49.5 parts, and water 16 parts were mixed/blended in an almighty Mixer (manufactured by Dalton K. K.), and pelletized by using an extrusion type pelletizer equipped with a screen having 0.8 mm apertures (BR-200, manufactured by Fuji Powdal K. K.). This pellet was dried at 50° C., to obtain a pellet 1.

EXAMPLE 4

Pellet 2

The thifluzamide obtained in Example 2 was processed like Example 3, to obtain a pellet 2.

COMPARATIVE EXAMPLE 1

Comparative Pellet

After dissolving thifluzamide 10 g in acetonitrile 160 ml at room temperature and agitating for 60 minutes, it was filtered through a 1 μm filter paper. After removing the acetonitrile from the filtrate by means of an evaporator, it was dried under a reduced pressure, to obtain thifluzamide.

The thus-obtained thifluzamide was processed like Example 3, to obtain a comparative pellet.

EXAMPLE OF TEST

Releasing Test of Pellet

Forty five milligrams each of the pellets 1 and 2 and comparative pellet were added in a beaker containing 1000 ml of hard water (hardness=10°) kept at a water temperature of 30° C. After standing calmly for 7 days, a portion of the solution was taken from the center portion of the beaker, and content of thifluzamide was analyzed, and percent of the thifluzamide being released was calculated by the following equation.

% Released=$A \times 100/B$

A: Amount (mg) of thifluzamide released in water
B: Content of thifluzamide (mg) in the pellet which was added in a beaker Results are presented in Table 1.

TABLE 1

|  | % Released on 7th day |
|---|---|
| Pellet 1 | 85 |
| Pellet 2 | 85 |
| Comparative pellet | 58 |

These data indicate that the rate of release of thifluzamide in water can be increased by using an agricultural chemical composition that contains the active carbon-treated thifluzamide as its effective ingredient.

We claim:

1. An agricultural chemical composition comprising thifluzamide treated with active carbon.

2. The agricultural chemical composition of claim 1 wherein the thifluzamide is obtained by dissolving thifluzamide in organic solvent and the resulting solution is treated with active carbon.

3. A process for preparing thifluzamide with improved release in water, comprising:

a) dissolving thifluzamide in an organic solvent, b) adding active carbon, c) removing the active carbon, d) removing the organic solvent by distillation, and e) crystallizing the thifluzamide.

4. The agricultural chemical composition of claim 2 wherein the amount of active carbon is 0.0001–0.5 part by weight per one part by weight of thifluzamide in the solution.

5. The process of claim 3 wherein the amount of active carbon is 0.0001–0.5 part by weight per one part by weight of thifluzamide in the solution.

6. The agricultural chemical composition of claim 2 wherein the solubility of thifluzamide in the organic solvent is at least 1.0 g/100 ml at 20° C.

\* \* \* \* \*